(12) United States Patent
Edmonson et al.

(10) Patent No.: US 6,967,428 B2
(45) Date of Patent: Nov. 22, 2005

(54) SELECTABLE REFLECTOR ARRAYS FOR SAW SENSORS AND IDENTIFICATION DEVICES

(75) Inventors: Peter J. Edmonson, Hamilton (CA); Colin K. Campbell, Ancaster (CA)

(73) Assignee: P. J. Edmonson Ltd., Hamilton (CA)

( * ) Notice: Subject to any disclaimer, the term of this patent is extended or adjusted under 35 U.S.C. 154(b) by 0 days.

(21) Appl. No.: 10/729,920

(22) Filed: Dec. 9, 2003

(65) Prior Publication Data

US 2005/0121999 A1    Jun. 9, 2005

(51) Int. Cl.$^7$ ............................ G01S 13/80; H04Q 5/22
(52) U.S. Cl. .................... 310/313 D; 342/51; 333/153; 333/154; 340/571.2; 340/825.34
(58) Field of Search ........................... 73/570; 342/42, 342/44, 51; 340/572.1, 825.34, 825.72; 310/313 B, 310/313 D; 333/150, 153, 154

(56) References Cited

U.S. PATENT DOCUMENTS

| | | | | |
|---|---|---|---|---|
| 4,361,026 A | * | 11/1982 | Muller et al. ............... | 73/24.01 |
| 4,378,168 A | * | 3/1983 | Kuisma et al. ............... | 374/28 |
| 5,321,331 A | * | 6/1994 | Baer et al. ............... | 310/313 D |
| 5,841,214 A | * | 11/1998 | Schmidt et al. .......... | 310/313 D |
| 5,966,008 A | * | 10/1999 | Maier et al. ................... | 324/96 |
| 6,084,503 A | * | 7/2000 | Ruile et al. ................. | 340/10.1 |
| 6,144,332 A | * | 11/2000 | Reindl et al. ................. | 342/42 |
| 2003/0231107 A1 | * | 12/2003 | Edmonson et al. ...... | 340/10.42 |

FOREIGN PATENT DOCUMENTS

JP              01260746 A   * 10/1989   ........... H01J 29/76

* cited by examiner

Primary Examiner—Hezron Williams
Assistant Examiner—Rose M. Miller
(74) Attorney, Agent, or Firm—Robert F. Delbridge (57) ABSTRACT

A surface acoustic wave sensor or identification device has a piezoelectric substrate, an interdigitated transducer (IDT) input/output mounted on a substrate for receiving a radio frequency (RF) signal and propagating a corresponding surface acoustic wave along a surface of the substrate. An IDT reflector array is mounted on the substrate and operable to receive a surface acoustic wave and reflect the surface acoustic wave in modified form back to the IDT input/output for transmission of a corresponding modified RF signal from the device. The IDT reflector array has at least one reflector segment whose reflectivity characteristics are controlled to control the nature of the modified RF signal.

10 Claims, 9 Drawing Sheets

SELECTABLE REFLECTOR ARRAYS FOR SAW SENSORS AND IDENTIFICATION DEVICES

FIELD OF INVENTION

The present invention relates to SAW sensors and identification devices.

BACKGROUND OF THE INVENTION

Surface acoustic wave (SAW) sensors and identification devices are passive radio frequency (RF) devices capable of exchanging information over both wired and wireless media depending upon the specific application.

SUMMARY OF THE INVENTION

According to the invention, SAW sensors and identification devices are configured with selectable reflector arrays which provide the capability of offering reflective segments of the reflector array, which consecutively contains multiple data bits of information within. As each SAW sensor or identification device is interrogated by an RF signal, the newly elongated reflected signal contains a data stream similar to the data selected within each reflective segment of the reflector array and is returned back to the interrogator.

The data embedded within the reflector array resembles a pulse position type of modulation (PPM) wherein a reflector segment within the array which is "on" reflects the interrogation signal and a reflector segment within the array which is "off" does not reflect the interrogation signal. This on/off state is achieved by controlling the load attached to the interdigital transducer (IDT) of the reflector segment. If the split finger electrode IDT load is open circuited, the IDT will reflect an incident SAW. Conversely, if the split finger electrode (IDT) load is shorted, the reflection capability of the IDT is greatly reduced. The reflector segment can also translate, by means of an altered magnitude and phase response, values of its load between the limits of an open circuit and a short circuit.

There are three ways of selecting the data of each reflective segment of the reflector array. The first is during the fabrication of the SAW device and is well suited for producing a random number of data bit configurations from a single fabrication process. All SAW devices are identically fabricated with all reflective segments set to "off". A further processing step would then involve the laser trimming and subsequent opening of a split finger pair of electrodes with any reflector segment to produce an "on" segment. Such laser trimming can be computer controlled to produce a selective batch of coded devices.

The second way also involves fabricating identical SAW devices, but with fluidic channels positioned over an "on" split finger pair of electrodes within each reflector segment. A conductive fluid would then be selectively positioned within certain fluidic channels which, in the limit, effectively short the split finger electrodes of the IDT to produce an "off" state. Result is a selectively coded reflective array. Such positioning of the conductive fluid within the fluidic channels may result from sensor attributes by an intelligent process or by a selective acoustic wave.

The third way is comparable to the classification of electrochemical microsensors which measure resistance or the ability to measure current through an analyte. This way is similar to the second except that the fluidic channel is continuous so that a fluid analyte can flow over the split finger electrodes. The fluid analyte can be controlled by a micropump or by electric fields such as electro osmotic flow or by surface acoustic waves. This allows the metallized split finger electrodes to behave as ion-selective electrodes (ISEs). The conductivity of the analyte effectively controls the load of the reflector segment, thereby producing a magnitude and phase response characteristic of the properties of the analyte. The polymeric ion-selective membrane can also be photo patterned within the split finger electrode region to provide conductor sensitivity for certain vapor or liquid analyte being sampled via the fluidic channel.

A major aspect of this invention is thus the use of selectable reflector segments. The reflectors are selectable by microfluidic or intelligent trimming techniques to select and control the reflection magnitude and phase characteristics of a split finger IDT. Several of these IDT's may be configured as part of a total reflective array which contains a modifiable coded sequence.

Such election and control of the modifiable coded sequence may be achieved by varying the conductivity of select pairs of split finger electrodes within the IDT's of the reflective array, which in effect alters the load resistance of the IDT'S, and which then alters the IDT's reflection properties to modify the coded sequence.

Invention enables manufacturing costs of SAW sensor and identification devices to be lowered by permitting the fabrication of identical devices and then selectively trimming certain reflector segments to produce a controlled batch of coded devices.

With the use of fluidic channels, the invention enables field selectable programming of the reflective segments which allows variable information from a single sensor, a network of sensors, financial smart card, or any other variable data apparatus including ZigBee applications to be entered into such reflective segments and then embedded into the reflected interrogation signal. The movement of the conductive fluid within the fluidic channels can be controlled by the attributes of the sensor or by an intelligent processor.

The invention is also applicable to the analyses of chemical materials in both laboratory and/or wireless applications. Since a SAW device is very small in profile and completely passive, a wireless electrochemical application will also work well as in-situ implants to monitor various chemical ionic responses.

The invention has various advantages. A first advantage is that a method is provided to lower the manufacturing costs by fabricating identical SAW devices and then implementing a computer controlled laser trimming process on certain split finger pairs of electrodes within selected reflective segments to produce a controlled batch of coded devices.

A second advantage is that its provides the ability of using sensor attributes such as pressure, temperature, centrifugal force and other physical characteristics of sensor transducers, including acoustic wave movement motion, to control the conductive fluid within the fluidic channels of the reflective array to provide a means of transcribing data to the device.

A third advantage is the ability of an analogue sensor to be interrogated by an RF signal and have the reflected RF signal turned back to the interrogator with the digital representation of the sensor embedded into it. The combination of the extended reflective array and the ability for the sensor attributes to turn "on" and "off" certain segments of the reflective array allows for a digitization of the sensor's analog quantity.

A fourth advantage relates to the ability of a reflective array to reflect an interrogation signal which is characteristic of the resisted properties of a vapor or liquid analyte. This allows the combination of SAW and microfluidic technologies to form an electrochemical sensor. The split finger electrodes of the SAW IDT and therefore the IDT's reflective signature react to chemical changes within the fluidic channel to produce an ion-selective electrode (ISE). Signal processing techniques performed at the interrogation unit would separate out the differences of the reflective signal to distinguish certain properties of the vapor or liquid analyte. This reaction may also implement a polymeric material within the fluidic and electrode regions to support ionic measurements.

BRIEF DESCRIPTION OF THE DRAWINGS

Embodiments of the invention will now be described, by way of example, with reference to the accompanying drawings, of which.

DESCRIPTION OF PREFERRED EMBODIMENTS

Figure 1:
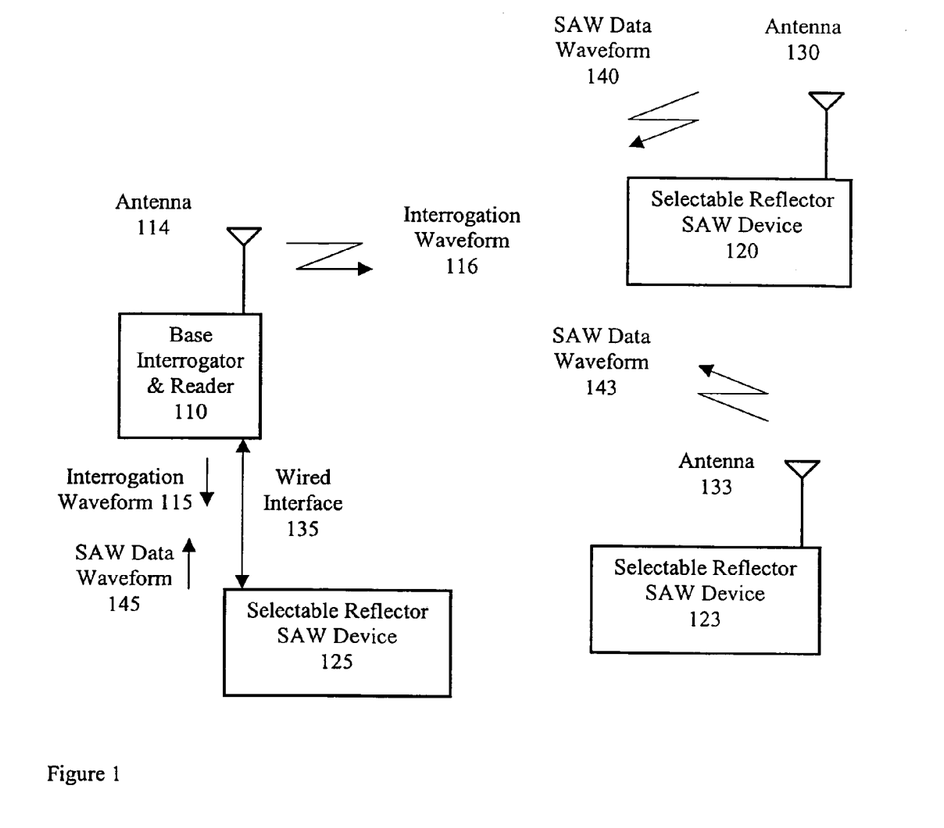
FIG. 1 is a block diagram of a simple system in accordance with one embodiment of the invention comprising a reader transceiver interrogating sole identification or sensor devices with an RF signal via a wired or wireless media.

Referring to the drawings, FIG. 1 shows a selectable reflective array which can be used for sensor and radio frequency identification devices (RFID). A base interrogator 110 initiates a sequence of events to query a remote SAW device 120 or, as part of a certain protocol, several remote SAW devices 123, 125. An intelligent process initiates a sequence of events where the base interrogator 110 transmits, via a base antenna 114 or wired interface 135, and interrogation signal 115, 116 which propagates towards the antennas 130, 133, of the remote SAW devices 120, 123, or is transmitted via the wired interface 135. Once received within the selectable reflector SAW device 120, 123 and 125, the interrogation acoustic signal is selectively reflected with encoded data and retransmits from the antennas 130, 133, or via the wired interface 135. The encoded data waveform 140, 143 and 145 returns to the base interrogation unit 110 via its antenna 114 or wired interface 135 to be processed. The data processed at the base unit represents the data embedded into the selectively reflective acoustic signal.

Figure 2:
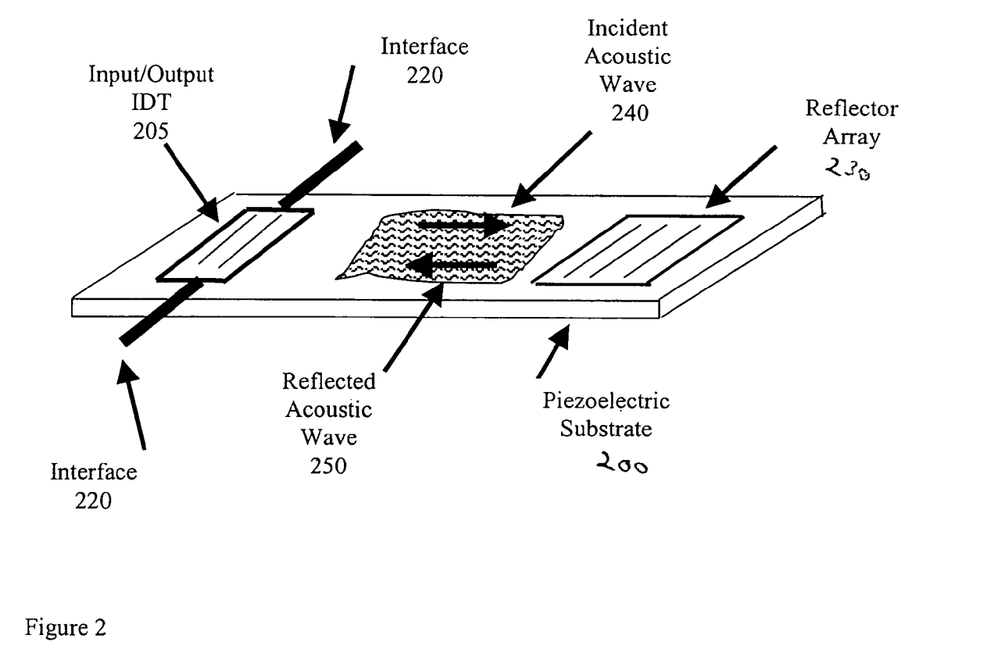
FIG. 2 is a schematic perspective view of basic elements of a wireless sole identification or sensor device.

A schematic view of the selectable reflector SAW device 120, 123, or 125 is shown in FIG. 2. The SAW circuit is fabricated on a piezoelectric substrate 200. The input/output IDT 205 has metallized finger electrodes placed on the surface of the piezoelectric substrate and receives the interrogation signal 116 via the attached interface 220 which may be an antenna or a wired interface. An electrical to acoustic wave transformation occurs within the IDT 205, and an incident acoustic wave 240 propagates along the piezoelectric substrate until it reaches a reflector array 230. The reflective array 230 has one or more reflective segments which, in turn, selectively reflect back the incident acoustic wave 240 to produce a concatenated reflected acoustic wave 250. This concatenated reflected acoustic wave contains reflected elements of the incident acoustic wave, depending upon the selectable load conditions of each reflective segment within the reflective array 230. The concatenated reflected acoustic wave 250 transforms within the input/output IDT 205 which converts the acoustic wave to electrical signals which are propagated back via the interface 220 to the base interrogation unit 110. Due to the harmonic content of the reflected acoustic wave 250, it would be desirable to implement single figure electrodes for the input/output IDT 205 to suppress the conversion of unwanted harmonic frequencies.

Figure 3:
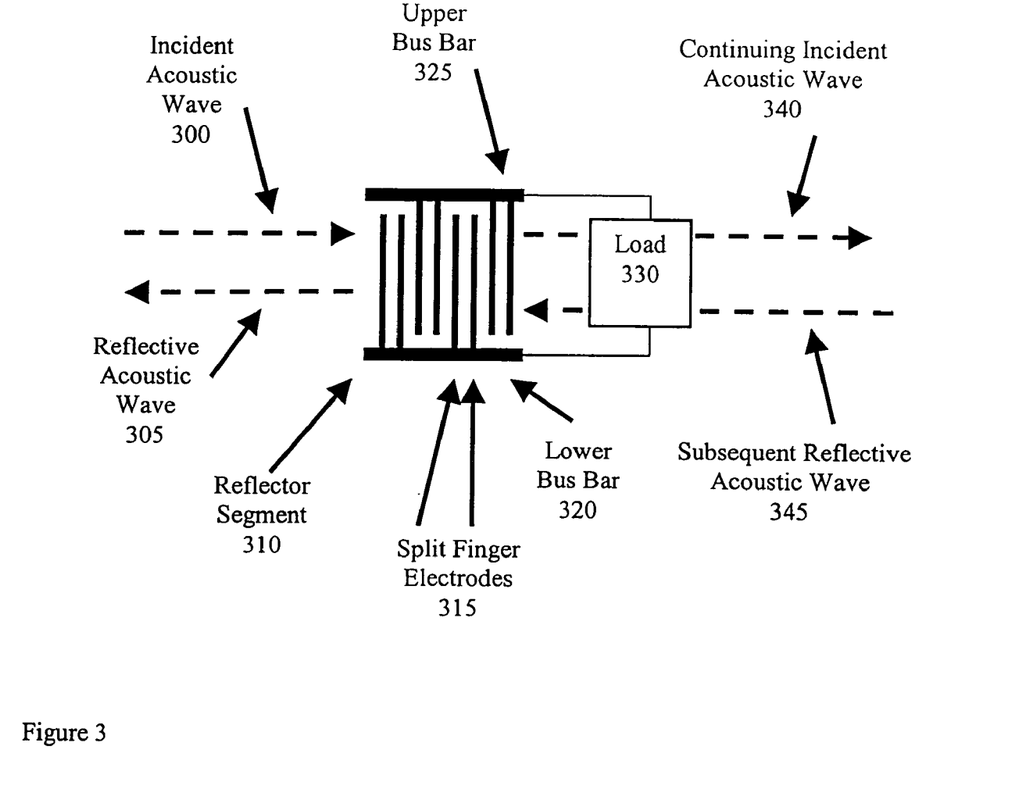
FIG. 3 is a diagrammatic view of elements of a split finger IDT reflector segment.

The composition of the elements of a split finger IDT reflector segment located within the reflector array 230 is illustrated in FIG. 3. An incident acoustic wave 300 approaches the reflector segment 310 which is fabricated such that the metallized split finger electrodes 315 are positioned in pairs which are alternately attached to the metallized lower bus bar 320 and to the upper bus bar 325. For a split finger IDT, each finger width and adjacent space is nominally an eighth-wavelength in width. A load element 330 is electrically connected to the lower bus bar 320 and to the upper bus bar 325. The characteristics of the reflector segment 310 can be predicted by the P-matrix notation for the reflection of a split finger IDT, which is terminated by a load admittance YL as shown in equation (1).

$$P22(YL) = P11, \ sc + \frac{2P13^2}{P33} + YL$$

at the limits, when $Y_L=0$ (open circuit), then the IDT achieves maximum reflection, ie. an "on" condition and, when $Y_L=\infty$ (short circuit), then a minimum of reflection occurs, ie. an "off" condition within the IDT. As $Y_L$ is varied between the limits of an open and a short circuit, P11 ($Y_L$) will vary both in magnitude and phase accordingly.

The effect of the load 330 then determines the presence of the reflected acoustic wave 305. Since there is not a total reflection of the incident acoustic wave 300, a continuing incident acoustic wave 340 continues to propagate on to the next reflector segment of the reflector array. Depending on subsequent load terminations, a reflective wave 345 is reflected back from the subsequent reflective segments.

Figure 4:
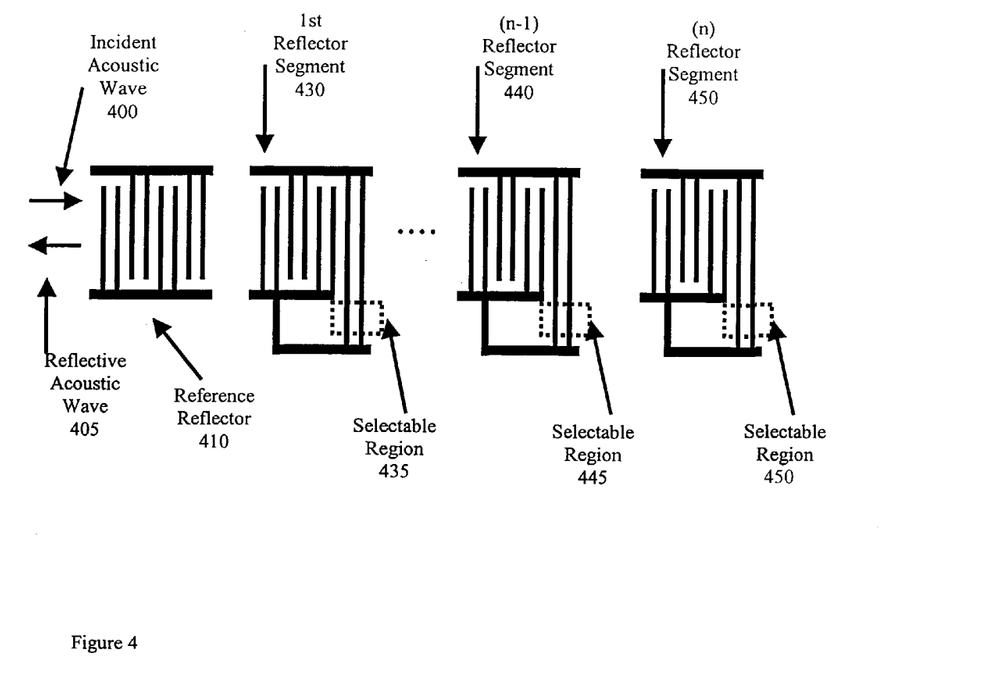
FIG. 4 is a similar view of elements of a selectable reflector array suitable for laser trimming.

The reflector array 230 is expanded in FIG. 4 to illustrate its various functional elements. An incident acoustic wave 400 first meets a reference IDT 410 which is continuously configured as a reflector by keeping its load as an open circuit. The open circuit load is accomplished by eliminating any electrical connection between the adjacent sets of split finger pairs of electrodes. The reference reflector 410 inserts the equivalent of a "start bit" in the reflective acoustic wave 405.

Other elements of this reflective array are the individual reflective segments 430, 440, 450, which are located linearly within the acoustic wave path. The number of reflective segments depends on the number of bits chosen for the specific sensor and RFID application. The reflective segments 430, 440, 450 within the reflector array are all fabricated as "off" segments, in that a selected pair of split finger electrodes act as a shorted load element electrically connecting the two bus bars 320, 325 and all of the electrode finger pairs together. These selected finger pairs are then exposed to selectable regions 435, 445, and 455 of the reflective segments 430, 440, and 450 respectively. During fabrication, a computer controlled trimming process selectively cuts the selective split finger electrodes to produce a controlled batch of coded reflector arrays which in effect produces a controlled batch of SAW senor and identification devices. The depiction of the selectable regions 435, 445, and 455 are shown as singular regions for each of the reflective segments 430, 440, and 450. However, in practice, the selectable regions can be replicated at each side or end of the IDT.

Figure 5:
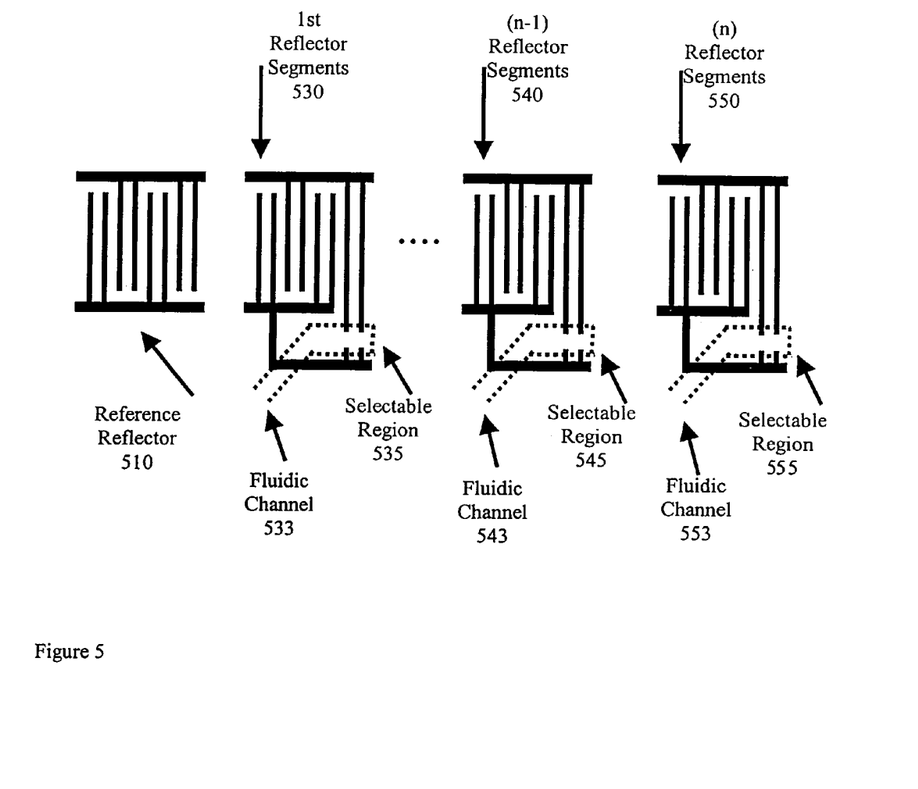
FIG. 5 is a similar view of elements of a selectable reflector array suitable for fluidic control.

An arrangement which allows for "field programming" of the reflector segments of the reflector array is illustrated in FIG. 5. The reference reflector 510 performs the same function of initiating an equivalent start bit as did the previous reference reflector 410 of FIG. 4. The remaining reflector segments 530, 540, and 550 are all fabricated as "on" segments, in that the effective load between the bus bars is an open circuit. Within the first reflector segment 530, there is located a selectable region 535 which contains an open pair of split finger electrodes and a fluidic channel 533. When a conductive fluid fills the fluidic channel 533, the conductive fluid effectively shorts out the pair of split finger electrodes within the selectable region 535. This in effect electrically connects the two bus bars and all of the electrode finger pairs together to reduce the reflective characteristics of the reflecting segment 530 to produce an "off" segment. Similar sequences can occur for reflector segments 540 and 550 with selectable regions 545 and 555 and fluidic channels 543 and 553 respectively.

Figure 6:
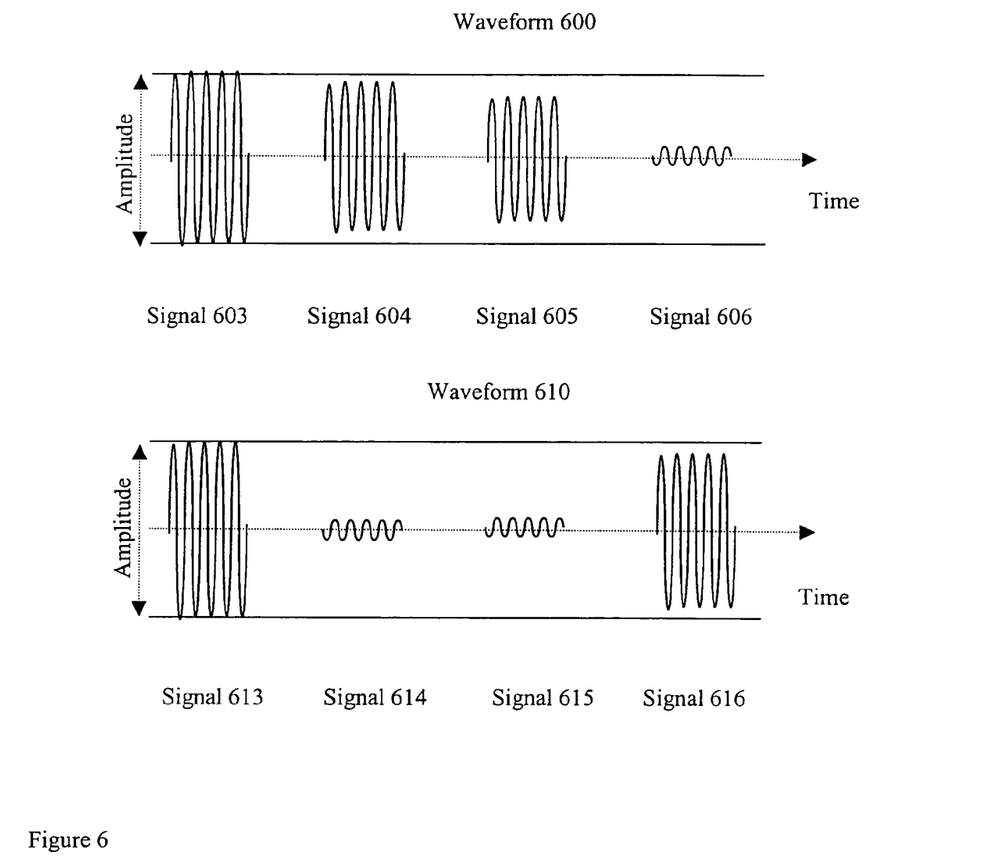
FIG. 6 shows magnitude and time diagrams of reflected SAW waveforms from a reflector array.

Diagrams showing amplitude versus time characteristics of the reflected acoustic waves are shown in FIG. 6. Both waveforms 600 and 610 can be the result of reflector arrays configured as in the computer aided trimming process shown in FIG. 4 or as a "field programmable" reflective array with the use of fluidic channels as shown in FIG. 5. For the first waveform 600 of FIG. 6, there are a total of four signals which indicate a reflective array with one reference reflector and three reflective segments. The signals are illustrated on a vertical amplitude and horizontal time axis. The first signal 603 is the reflected response from the reference reflector 410 or 510 shown previously. The next signal 604 is the result of the incident wave continuing through the reference reflector 410 or 510 and reflecting from the first reflector segment 430 or 530.

The load for the reflecting segments 430 or 530 must be an open circuit so maximum reflection occurs. It should be noted that the amplitude of signal 604 is slightly smaller than that of signal 603 due to losses within the system. Similarly, signal 605 is the result of the incident wave continuing through the first reflective segment 430 or 530 and reflecting from the n−1 reflector segment 440 or 540. The load for the two reflecting segments 440 or 540 must also be an open circuit so maximum reflection occurs. It should again be noted that the amplitude of signal 605 is slightly lower than that of the preceding signal 604 due to losses within the system. Similarly, signal 606 is the result of the incident wave continuing through the n−1$^{th}$ reflective segment 440 or 540 and reflecting from the n$^{th}$ reflector segment 450 or 550.

The load for the reflecting segments 450 or 550 must be a short circuit so a minimum of reflection occurs. It should again be noted that the amplitude of signal 606 is much lower than that of the preceding signal 604 due to the inability of the n$^{th}$ reflector segment 450 or 550 to reflect an incident wave.

Similarly, for waveform 610, signal 613 is also the result of a reference reflector segment, with signal 614 and signal 615 being the result of having reflector segments configured with a short circuit load, and with signal 616 resulting from having a reflector segment configured with an open circuit load. The waveform 600 and 610 can be construed as digital representations of successive load conditions, namely 1 1 1 0 and 1 0 0 1 respectively.

Figure 7:
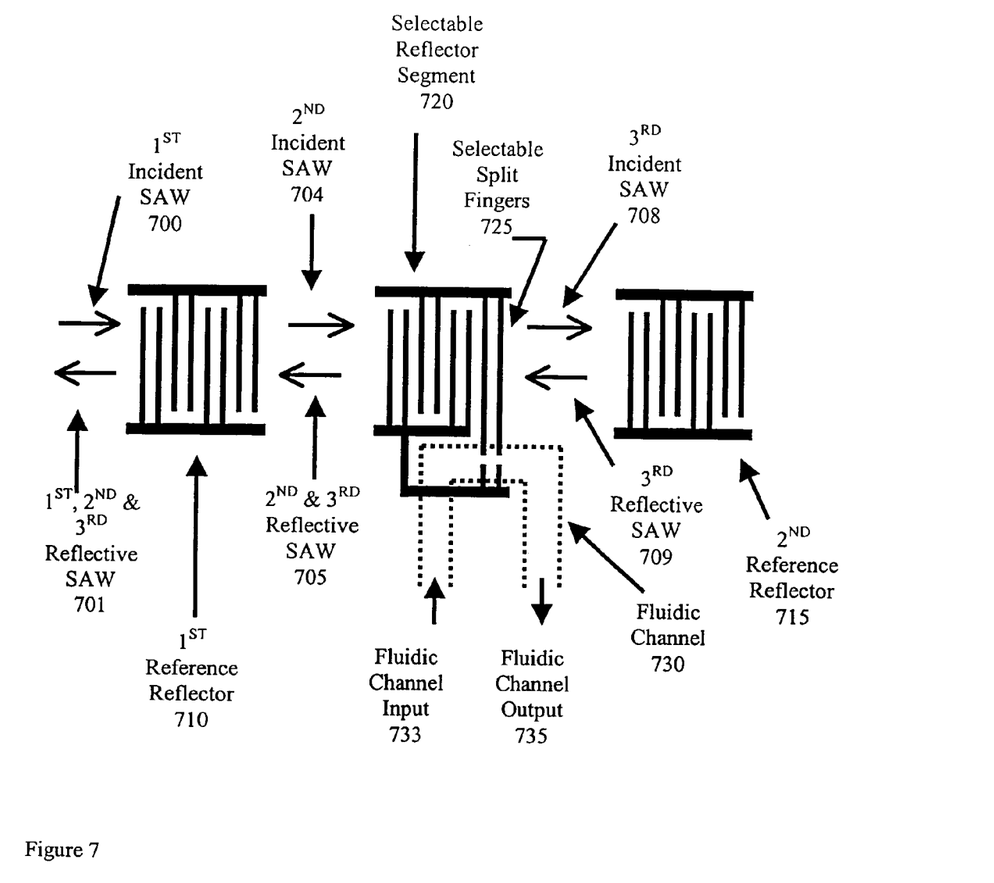
FIG. 7 is a diagrammatic view of elements of a selectable reflector array suitable for a chemiresistor.

This invention can readily be adapted to combine SAW and microfluidic technologies to form an electrochemical ion-selective sensor. FIG. 7 illustrates how a reflective array can be arranged with three reflector segments to create a SAW based microfluidic sensor. This sensor would provide the means of sensing both vapor and liquid analyte samples. This can be accomplished by using photolithographic techniques to impose a sorptive polymeric material within the fluidic channel 730 and the selectable split finger electrodes 725. The incident surface acoustic wave 700 is excited from an input/output IDT 205 of FIG. 2. The IDT 205 need not be attached to an antenna as this use could be implemented in a wireless situation or a laboratory benchtop electrochemical senor wired via a suitable interface to an intelligent processor.

The incident SAW 700 will reflect from the first reference reflector 710 to produce a first reflective SAW 701. A continuing second incident SAW will propagate through the first reference reflector 710 to interact with the selectable reflector segment 720. The conductivity of the sample fluid entering the fluidic channel 733 and exiting the fluidic channel 735 would determine the load component $Y_L$ of equation (1). For a fluid sample low in ions, presenting a low conductivity case, the selectable reflector segment 720 will produce a maximum reflective SAW 705 from the second incident SAW 704. For a fluid sample containing various concentrations of ions, the value of $Y_L$ will vary, therefore producing varying magnitude and phase values of the reflected SAW 705. At the limit of maximum concentration of ions, YL is a short circuit, therefore minimizing the second reflected SAW 705. A continuing third incident SAW will propagate through the selectable reflector segment 720 to interact with the second reference reflector 715. The incident SAW 708 will reflect from the second reference reflector 715 to produce a third reflective SAW 709. All reflective SAW components 701 will propagate towards the input/output IDT 205.

Figure 8:
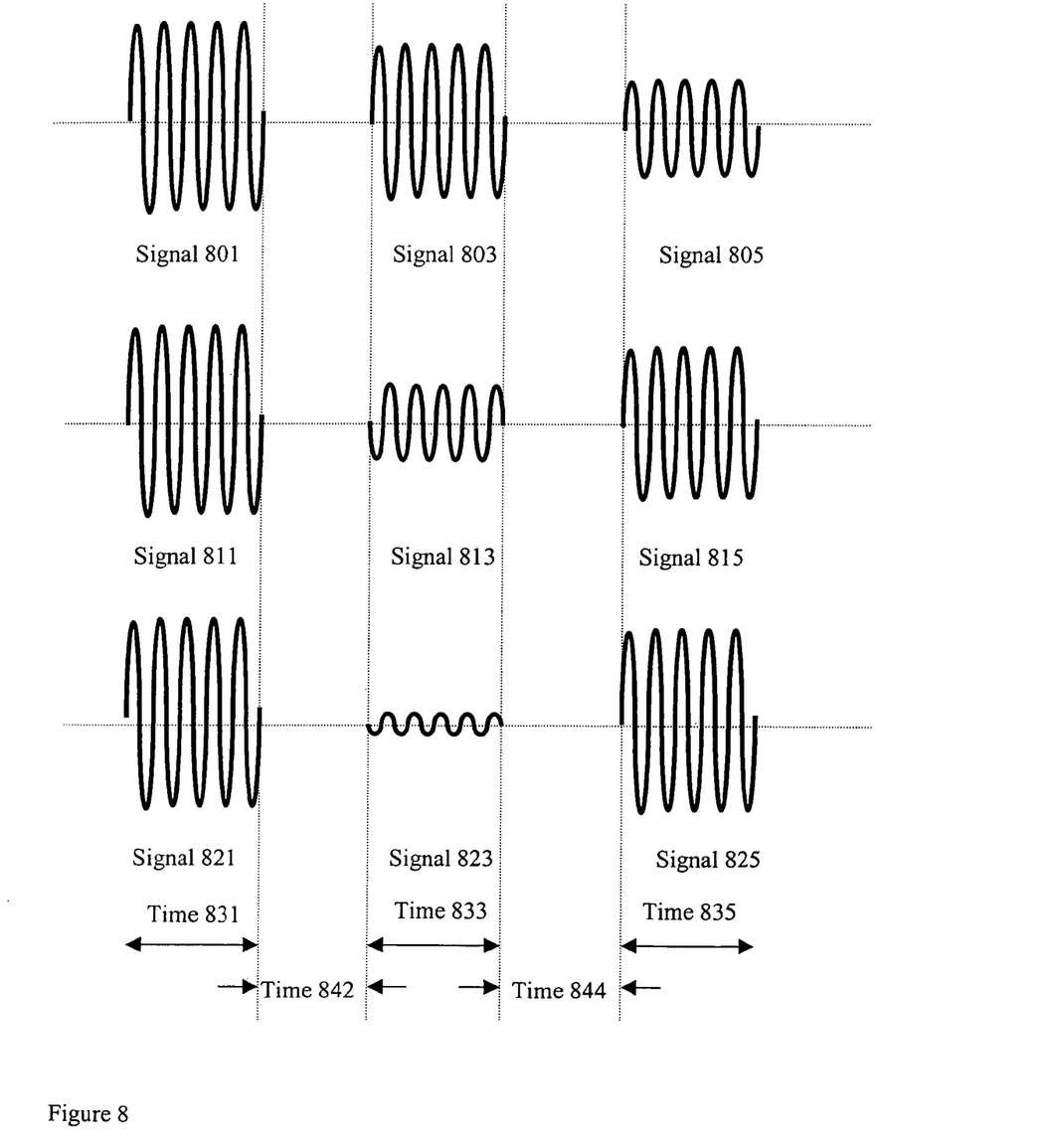
FIG. 8 shows magnitude and time diagrams of reflected sole waveforms applied to a chemiresistor type sensor.

Three examples of the magnitude versus time responses of the electrochemical sensor of FIG. 7 are illustrated in FIG. 8 for various ion concentrations of the sample analyte. In the first sequence, signals 801 and 805 are from reference reflectors, and signal 803 has a magnitude and phase representative of the reference signals 801 and 805 to indicate that the analyte being measured has minimal conductivity. The second sequence sampled signal 813 shows a marked difference in both magnitude and phase with respect to the reference signals 811 and 815. Signal processing techniques can be implemented to enhance this difference, which can then be extrapolated using equation (1) to determine the load value of $Y_L$, which in effect determines the ionic composition of the sample analyte. The final sequence shows how the signal 823 compares with the two reference signals 821 and 825 to indicate a reflection segment with a minimum of reflection which tends, in the limit, to indicate a short circuit $Y_L$. This condition represents a sampled analyte which has maximum ionic concentration. The time slots indicated by 831, 833 and 835 represent the time duration of the reflected acoustic waves and are indicative of the spatial length of the interrogation pulse 116 shown in FIG. 1. The time spacing between reflected pulses 842 and 844 are dependent on the spacing of the reflector segments of the reflector array.

Figure 9:
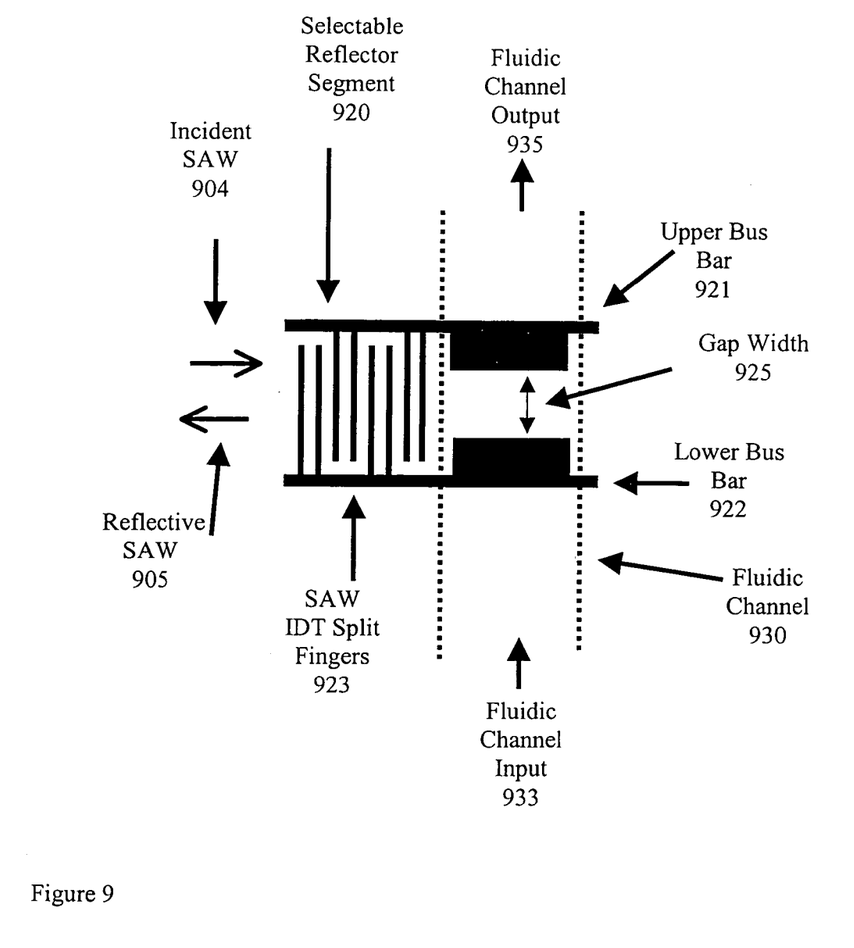
FIG. 9 is a diagrammatic view of elements of a selectable reflector with modified metallized regions within fluidic channels.

The reflector segment 720 shown in FIG. 7 has typical split finger dimensions of approximately 0.21 μm, assuming a 0.5 metallization ration, an operating frequency of 2,400 MHZ and a 128° YX-LiNbO$_3$ substrate. The fluidic channel 730 is dimensioned to contained one pair of split fingers. Analyte with dimensions greater than the width of the split fingers will possibly have difficulty traversing the fluidic channel and providing adequate conductivity. A modified reflector segment 920 and a larger fluidic channel 930 which overcome this problem are shown in FIG. 9. The width of both the upper bus bar 921 and lower bus bar 922 within the fluidic channel 930 can be varied in width during manufacturing. The width of these modified metallized regions of the upper bus bar 921 and lower bus bar 922 produce a gap width 925 which can be arranged to be suitable in dimensionality to the selected analyte. This configuration would still allow a sorptive polymeric material to be placed within the fluidic channel 930. The flow of analyte into the fluidic channel input 933 and out the fluidic channel output 935 can be controlled by an intelligent process using pressure, electric fields such as electro osmotic flow or surface acoustic waves.

The advantages of the invention will now be readily apparent to a person skilled in the art from the above description of preferred embodiments. Other embodiments and advantages of the invention will also now be readily apparent to a person skilled in the art, the scope of the invention being defined in the appended claims.

What is claimed is:

1. A surface acoustic wave sensor or identification device having:
    a piezoelectric substrate,
    an interdigitated transducer (IDT) input/output mounted on a substrate for receiving a radio frequency (RF) signal and propagating a corresponding surface acoustic wave along a surface of the substrate,
    an IDT reflector array mounted on the substrate and operable to receive said surface acoustic wave and reflect said surface acoustic wave in modified form back to the IDT input/output for transmission of a corresponding modified RF signal from the device,
    said IDT reflector array having at least one reflector segment whose reflectivity characteristics are controlled to control the nature of the modified RF signal, and
    said at least one reflector segment having a fluidic chamber which in use contains fluid operable to control the nature of the reflected surface acoustic wave and hence the nature of the modified RF signal.

2. A sensor or identification device according to claim 1 wherein the reflectivity characteristics of said at least one reflector segment are controlled during the manufacturing process to give the device a unique modified RF signal.

3. A sensor or identification device according to claim 1 wherein the reflectivity characteristics of said at least one reflector segment are controlled by a variable load externally thereof.

4. A sensor or identification device according to claim 3 wherein the external load is a transducer.

5. A sensor or identification device according to claim 4 wherein the sensor is an analog sensor.

6. A sensor or identification device according to claim 1 wherein the chamber has an inlet and an outlet whereby in use the fluid flows through the chamber from the inlet to the outlet.

7. A sensor or identification device according to claim 1 wherein said at least one reflector segment has at least one pair of interdigitated fingers which communicate with said chamber.

8. A sensor or identification device according to claim 7 wherein said at least one pair of interdigitated fingers project into the chamber.

9. A sensor or identification device according to claim 7 wherein said at least one pair of interdigitated fingers are connected to respective bus bars and the chamber is formed between extensions of said bus bars.

10. A sensor or identification device according to claim 1 wherein the chamber has a wall with a conductive material thereon, the conductivity of the material being varied by variation of the nature of the fluid in the chamber.

* * * * *